United States Patent
Nguyen et al.

(10) Patent No.: US 6,797,944 B2
(45) Date of Patent: Sep. 28, 2004

(54) LASER DESORPTION AND DETECTION OF EXPLOSIVES, NARCOTICS, AND OTHER CHEMICAL SUBSTANCES

(75) Inventors: Dao Hinh Nguyen, Ottawa (CA); Stewart Berry, Ottawa (CA); David L. Christensen, Kingston (CA); Chris Klymowsky, Ottawa (CA)

(73) Assignee: Control Screening, LLC, Fairfield, NJ (US)

( * ) Notice: Subject to any disclaimer, the term of this patent is extended or adjusted under 35 U.S.C. 154(b) by 167 days.

(21) Appl. No.: 10/062,135

(22) Filed: Feb. 1, 2002

(65) Prior Publication Data

US 2004/0169845 A1 Sep. 2, 2004

(51) Int. Cl.$^7$ ................................. H01J 49/40
(52) U.S. Cl. ........................ 250/286; 356/36
(58) Field of Search ............. 250/281, 287, 250/288, 286; 436/174, 177, 161, 173, 106; 422/89, 100; 356/36

(56) References Cited

U.S. PATENT DOCUMENTS

| | | | |
|---|---|---|---|
| 4,220,414 A | | 9/1980 | Barringer .................... 356/318 |
| 4,925,523 A | * | 5/1990 | Braren et al. ................. 216/66 |
| 4,941,162 A | | 7/1990 | Vartsky et al. ................ 378/3 |
| 4,987,767 A | | 1/1991 | Corrigan et al. ........... 73/23.36 |
| 4,988,879 A | | 1/1991 | Zare et al. .................... 250/423 |
| 5,092,157 A | * | 3/1992 | Achter et al. ................. 436/156 |
| 5,135,870 A | * | 8/1992 | Williams et al. ............. 250/288 |
| 5,241,179 A | * | 8/1993 | Carrieri .................... 250/341.6 |
| 5,268,302 A | * | 12/1993 | Rounbehler et al. .......... 422/89 |
| 5,364,795 A | | 11/1994 | Sausa et al. ................. 436/106 |
| 5,395,589 A | | 3/1995 | Nacson ........................ 422/88 |
| 5,416,321 A | * | 5/1995 | Sebastian et al. ........... 250/288 |
| 5,426,056 A | * | 6/1995 | Nacson ........................ 250/281 |
| 5,585,575 A | * | 12/1996 | Corrigan et al. ............. 73/23.2 |
| 5,669,979 A | * | 9/1997 | Elliott et al. .................... 134/1 |
| 5,760,898 A | | 6/1998 | Haley et al. ................. 356/318 |
| 5,906,946 A | | 5/1999 | Sausa et al. ................. 436/116 |
| 5,912,466 A | | 6/1999 | Funsten et al. ............. 250/372 |
| 6,058,159 A | | 5/2000 | Conway et al. ............... 378/68 |
| 6,074,608 A | | 6/2000 | Matz .......................... 422/83 |
| 6,137,110 A | * | 10/2000 | Pellin et al. ............. 250/423 P |
| 6,150,630 A | | 11/2000 | Perry et al. ............ 219/121.68 |
| 6,295,860 B1 | | 10/2001 | Sakairi et al. ............. 73/23.41 |
| 6,610,977 B2 | * | 8/2003 | Megerle ..................... 250/287 |
| 2003/0010907 A1 | * | 1/2003 | Hayek et al. ............... 250/281 |
| 2003/0152186 A1 | * | 8/2003 | Jurczyk et al. ............. 376/109 |

OTHER PUBLICATIONS

A. Clark et al., *American Institute of Physics*, 1995, 259–262.

(List continued on next page.)

*Primary Examiner*—Michael P. Stafira
*Assistant Examiner*—Juan D Valentin, II
(74) *Attorney, Agent, or Firm*—Ernest D. Buff & Associates, LLC; Ernest D. Buff; Gordon E. Fish

(57) ABSTRACT

A compact scanning apparatus includes an optical system to deliver a beam of pulsed infrared laser light that illuminate an interrogation area of a surface. The illumination has sufficient intensity and duration to cause selective ablation of molecules of a contraband substance present on the surface without substantially damaging the surface. A collection system collects at least a portion of the ablated molecules and transfers them to a chemical analysis system having a detector. In response to the presence of a wide variety of contraband substance molecules, the detector outputs an electrical signal that activates an audible or visible alarm. Automated screening is provided in an accurate, reliable manner that virtually eliminates the vagaries of human performance. False alarms are reduced. Detection efficacy is increased. A traceable residue of the detected contraband is left on the article for subsequent forensic analysis.

53 Claims, 2 Drawing Sheets

OTHER PUBLICATIONS

M. Handschuh et al., *Appl. Surface Science*, 1999, 137, 125–135.

F. Heresch et al., *Anal. Chem.*, 1980, 52, 1803–1807.

S.D. Huang et al., *Appl. Spectroscopy*, 1987, 41, 1371–1376.

G.R. Kinsel et al., *J. Phys. Chem.*, 1991, 95, 7824–7830.

P. Kolla, *Angew. Chem.*, 1997, 109, 828–839. Translated by Dr. W.C. Wilisch.

J.S. Morgan et al., *John Hopkins APL Technical Digest*, 1999, vol. 20, No. 3, 389–395.

D. Orenstein, "How a Bomb Sniffer Works", Business20. Available at http://www.business20.com, Nov. 2001.

D.J. Phares et al., *Journal of Forensic Sciences*, 1999, 774–784.

Th. Roch et al. "Laser–Based Ion Mobility Spectrometry As An Analytical Tool For Soil Analysis", International Society for Ion Mobility Spectrometry, 1998, pp. 43–47.

P. Sperry "Homeland Insecurity", WorldNetDaily. Available at http://www.worldnetdaily.com, Mar. 2002.

C. Yates "Jane's Airport Security–Standard & Technology (continuted)", Market Review. Available at http://www.jan-es.com, Aug. 1999.

L. V. Zhigilei et al., *Appl. Surface Science*, 1998, 127–129, 142–150.

L. V. Zhigilei et al., *Appl. Phys. Lett.*, 1999, vol. 74, No. 9, 1341–1343.

\* cited by examiner

LASER DESORPTION AND DETECTION OF EXPLOSIVES, NARCOTICS, AND OTHER CHEMICAL SUBSTANCES

BACKGROUND OF THE INVENTION

1. Field of the Invention

This invention relates to the field of scanner apparatus and methods; and more particularly to inspection systems that scan luggage and cargo to detect residues of explosives or other contraband materials.

2. Description of the Prior Art

In recent years, the prevalence of criminal activity that entails transportation of weapons and contraband materials has been a significant public concern. It has thus become vital to develop systems for detecting the presence of these materials, both when shipped as luggage or cargo and when carried by an individual. Of particular concern is the need to detect items used as weapons by terrorists, including ordinary firearms and knives, items such as explosive or incendiary substances, and materials which present biological, chemical or radiological hazards to people and property. The detection of illicit drugs and narcotics being transported is also of concern.

The detection of contraband in the context of air and rail transportation is especially challenging, given the need to examine large numbers of people and articles of luggage and cargo within acceptable limits on throughput and intrusiveness. Although physical inspection is a widely practiced and important technique, it is slow, cumbersome, labor intensive, and dependent on the alertness and vigilance of the inspector.

Automated systems that screen for contraband have been sought for many years. Various techniques have been proposed to detect contraband objects and materials either directly or indirectly. Magnetometry is widely used, and is sometime effective in detecting metallic objects carried by persons, but is not suited for screening cargo, which legitimately may contain large amounts of metal. Nuclear techniques, including x-ray, gamma-ray, neutron activation, and nuclear magnetic resonance methods, are applicable for screening inanimate objects, but pose risks that generally preclude their use for screening humans. In some cases, they are able to detect metallic objects, including weapons and ancillary devices such as wires, power supplies, batteries, and triggering mechanisms for explosive devices. However, there increasingly exist threats posed by explosives associated with largely non-metallic objects, which the aforementioned methods are less able to detect. The advent of modern plastic explosives presents an especially significant threat. Even a modest, readily concealable amount of these substances can cause a substantial explosion. Moreover, miscreants have become increasingly adept at disguising weapons and explosive devices as ordinary, innocuous objects. As a result, more refined indirect methods for detection of explosives are urgently sought.

Many of the indirect methods rely on the presence of vapor emanating from suspect material. One such indirect method, widely used in law enforcement, employs dogs trained to sniff preferentially for explosives, drugs, and the like. The remarkable olfactory sensitivity of dogs has been known and exploited for centuries. However, they are subject to fatigue, behavior variations, and the need for careful handling, training, and reinforcement from their masters. It therefore remains highly desirable to have luggage scanning systems that are not subject to these limitations. Also needed are luggage and cargo scanning systems that rapidly and accurately discriminate among different substances and indicate the quantity and location of a critical substance.

The task of indirectly detecting the presence of suspect materials is further complicated by their wide variability in vapor pressure. Some explosives, including nitroglycerin, dynamite, EGDN, and EGTN, are comparatively volatile, exhibiting significant vapor pressure at room temperature. DNT and TNT have lower, but still appreciable room-temperature vapor pressure. However, some of the most critical materials for which detection is sought, e.g. drugs, such as cocaine and heroin, and plastic explosives, such as SEMTEX and C-4, are far less volatile, having room temperature vapor pressures as much as ten million times lower. It is virtually impossible to detect vapor naturally emanating from these low volatility materials. They are even more difficult to detect if sealed inside luggage or packaging.

It is known that certain contraband materials for which detection is sought are inherently sticky. This characteristic is a notable property of many plastic explosives. As a result, particulate residues are likely to be present (i) on the hands of a person who has even casually handled the contraband, even after repeated hand washing, (ii) in fingerprints on surfaces such a person has subsequently touched, and (iii) as cross-contamination on the surface of a vehicle, shipping container, or luggage in which the material has been placed. For example, a measurable amount of ammonium nitrate (AN) residue has been found on the lease documents for rental trucks; and significant amounts of the explosives PETN (pentaerythritol tetranitrate) and/or AN have also been found on clothing and inside vehicles of suspects in two well-publicized bombings. Therefore, explosive residue will likely persist in large amounts on the explosive packaging and its environs, as well as on the individuals involved in building, handling, and transporting the explosive device, thereby providing an avenue for detection of the presence of explosives. The detection of even trace residues of critical substances on a person, article, or vehicle suggests a strong likelihood of association with illicit activity warranting further investigation.

The dual challenges of sample collection and analysis continue to impede development of satisfactory screening systems for these materials. As previously described, many of the materials whose detection is most critical have extremely low vapor pressure. The equilibrium concentration in the atmosphere near a contaminated fingerprint may be only parts per billion or trillion, a value too low for known detection schemes. Hence, previous detection methods have generally required use of mechanical means for collecting and/or concentrating a sample to achieve delectability. In some cases, disposable swabs or wipes of dry paper or cloth are rubbed by an operator against luggage or shipping containers to pick up detectable amounts, if any, of particulate residue. Such wipes may also be wetted with a solvent to facilitate residue pickup. In either case, the wipe is subsequently transferred to a suitable detection system for chemical analysis. However, known wipe systems have a number of significant limitations. They generally require an operator and are not conveniently adapted to automation. Their throughput is limited by the cumulative time needed for the essential multiple operations—in addition to the actual analytical time, the process requires the prior intermediate steps of wiping the article under test and transferring the wipe to the detection system. The detection efficacy and success of wipe systems is generally dependent on human factors. Stress and the frequent confusion extant in a busy public facility may cause an operator to fail to carry out an adequate sampling. The wiping operation frequently fails to cover a sufficiently representative portion of an article to insure that whatever residues are present are actually captured. Lint, dirt, solvent, and other extraneous material of no interest are inevitably introduced into the detection system, reducing its sensitivity by diluting the concentration of the analyte and necessitating frequent, non-productive cleaning operations.

Other known systems have employed mechanical brushing or shaking of articles or impingement of a compressed gas stream to dislodge residue particles. While these methods are more amenable to automation than wiping-based methods, they still are not sufficiently fast and efficacious for the demanding requirements of inspecting items to be carried as cargo or hand luggage on aircraft, for example. Furthermore, regulation of the pressure and volume of the gas stream is a significant challenge, as the flow must be sufficient to dislodge particles but not so high that it is not possible to capture what is removed.

Systems have also been proposed for detecting the presence of residues on a human subject passing through a tunnel-like portal. The portal may include means for flowing gas across the subject to dislodge particulate residues, collecting the gas, filtering or otherwise concentrating the particulates to above a detection limit, and passing the concentrated sample to a suitable detector. However, improvement in these systems is still desired. Flowing gas is at best an inefficient vehicle for collecting adequate sample. Disruptions of the airflow owing to the motion of subjects passing through the portal further compromise sample collection. In addition, the need to pre-concentrate a sample limits the analysis rate, making it difficult to reliably associate detection of contraband substances of interest with a specific person passing through the sampling portal.

Each of the indirect screening systems previously discussed requires means for sample collection and analysis that discriminate suspect substances from components normally present in the atmosphere. To be effective, the sample collection and analysis means must additionally discriminate suspect substances from the myriad of vapors produced by items of ordinary commerce.

A number of vapor detection methods have been proposed. These vapor detection methods have found use in laboratory analysis. Among them are electron capture detection, gas chromatography detection, mass spectrometry detection, plasma chromatography detection, bio-sensor detection and laser photoacoustic detection.

There have also been suggested systems for detecting explosive residues that do not rely on vapor detection. One example is the use of a controlled burst of laser radiation to induce selective deflagration or micro-detonations of explosive residues on the surface of an article. The resulting reaction produces an optical signature characteristic of the explosive residue. The system relies on detection of this optical signature. As used herein, the term "deflagration" means a slow chemical oxidation of the material, with a burn front which propagates at less than the velocity of sound. The term "detonation" as used herein means a reaction similar to deflagration that occurs at a much faster rate. Detonation is characterized by wave propagation at a supersonic rate with respect to the unreacted material.

Notwithstanding the aforementioned schemes both for sample collection and analysis, there remains a need in the art for integrated systems capable of reliably, accurately, and rapidly detecting the presence of contraband substances, especially explosives, accelerants, and illicit drugs. More particularly, there is need for systems that are readily automated for semi-continuous or continuous inspection and detection of the presence of residues of such materials on luggage, cargo, vehicles, freight containers, and related items. Such systems are highly sought, especially in the context of airport screening, but would be equally valuable for courthouses, stadiums, schools, government offices, military installations, correctional institutions, and other public venues that might be targets of terrorist or similar criminal activity.

SUMMARY OF THE INVENTION

The present invention provides a compact scanning system that rapidly detects the presence of a wide variety of contraband substances in an accurate, reliable manner. The system rapidly and accurately discriminates among different substances and provides quantitative indication of the amount and location of a critical substance. It is especially well suited for use in applications which require high throughput and accuracy, such as security screening associated with airline and other forms of public transportation.

Advantageously, the system provides for automated screening. It automatically scans substantially the entire exterior surface of luggage and other hand-carried personal items, as well as cargo, without the need for hand wiping or sampling by an operator or other physical contact. Vagaries of human performance are virtually eliminated, and detection efficacy is improved. The system's greater speed, accuracy, reliability, and flexibility, as well as its lower cost, and expanded range of detectable substances overcome problems associated with commercial scanning systems. Importantly, the system of this invention markedly reduces or eliminates false alarms while maximizing detection sensitivity for actual contraband. Following detection of contraband, a traceable residue thereof is left on the article for use in subsequent forensic analysis by law enforcement or other agencies.

In one aspect the invention provides an apparatus for non-destructively detecting the presence of a contraband substance on a surface of an object. Generally stated, the apparatus comprises an infrared laser adapted to emit light. An optical system delivers a beam of light emitted from the infrared laser to illuminate an interrogation area of the surface. The illumination has sufficient intensity and duration to cause selective desorption of molecules of said contraband substance present on said surface without damaging the surface. A collection system collects at least a portion of the desorbed molecules. A chemical analysis system is associated with said collection system. The chemical analysis system has a detector responsive to the presence in the collection system of the desorbed molecules. The detector is adapted to output an electrical signal representative of the presence of the contraband substance. A signal means is connected to the chemical analysis system operates in response to the output of said electrical signal to provide an audible or visible alarm.

In another aspect, the invention provides a method for detecting the presence of a preselected contraband substance on a surface of an object. Generally stated the method comprises the steps of (a) illuminating an interrogation area of the surface with a beam of light emitted from an infrared laser, the illumination having sufficient intensity and duration to cause selective desorption of molecules of the contraband substance present on the surface without damaging the surface; (b) collecting at least a portion of the desorbed molecules in a collection system; (c) analyzing the portion in a chemical analysis system, the system being associated with the collection system and comprising a detector responsive to the presence in the chemical analysis system of the contraband substance; (d) outputting an electrical signal representative of the presence of the contraband substance; and (e) activating signal means operably connected to said chemical analysis system in response to the output of said electrical signal, to thereby provide an audible or visible alarm.

BRIEF DESCRIPTION OF THE DRAWINGS

The invention will be more fully understood and further advantages will become apparent when reference is had to the following detailed description of the preferred embodiments of the invention and the accompanying drawings, wherein like reference numerals denote similar elements throughout the several views and in which.

DESCRIPTION OF THE PREFERRED EMBODIMENTS

Figure 1:
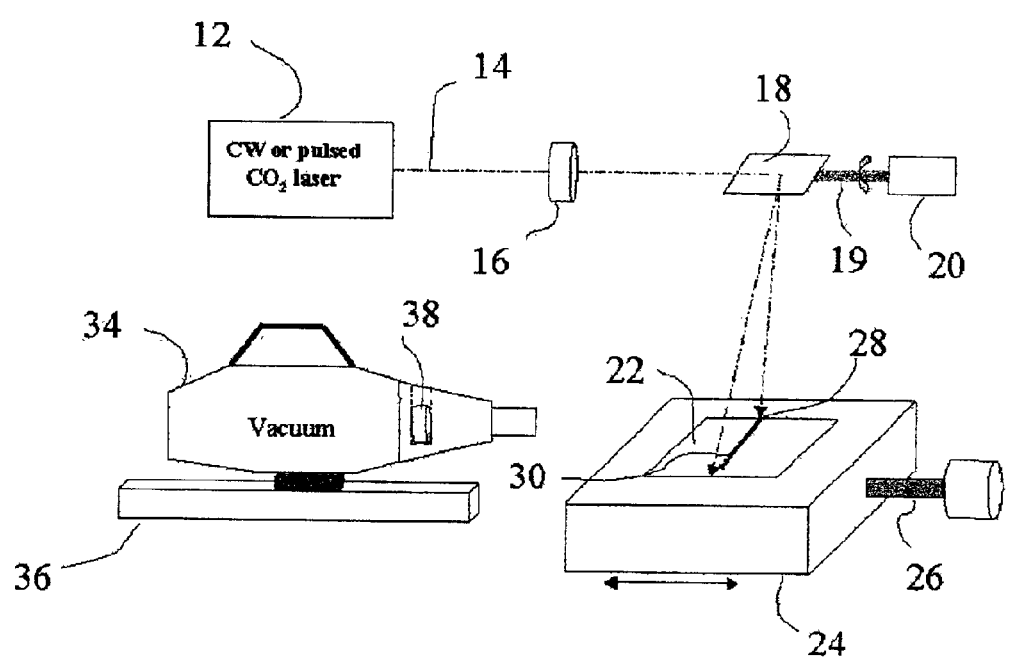
FIG. 1 is a perspective view of an explosive detection system of the invention.

The present invention is directed to a method and apparatus for the detection of contraband substances on the surface of objects. Generally stated, a beam of infrared laser light is impinged on an interrogation area on the surface to be scanned to cause desorption or ablation of molecules or particles of the contraband substance. The portion of the contraband substance that is removed is sufficient to be detectable. The specific amount that must be removed to effect detectability depends both on the specific material and the chemical analysis system employed, but may be as low as the sub-nanogram level. The interrogation area may be substantially the spot size of the beam. Alternatively the beam may be variably deflected or the object moved to vary the point of impingement, thereby extending the interrogation area generally to a linear region or an extended, two-dimensional area. It is preferred that the interrogation zone comprise at least a substantial portion of the object under scrutiny. The ejected material is collected in a collection system and analyzed by a chemical analysis system adapted to detect the presence of at least one contraband substance. An audible or visual indication is provided upon detection of a contraband substance. The detection system of the invention can detect the presence of a wide variety of contraband substances. As used herein, the term "contraband" is intended to denote substances or articles whose transportation or possession is forbidden or improper. A wide variety of substances or articles may be considered as contraband, including non-exclusively: firearms and similar weapons; explosives and explosive devices; incendiaries, propellants, and accelerants; drugs such as heroin, cocaine, opium and its derivatives and other narcotics, cannabis (including marijuana and hashish), amphetamines and barbituates; hallucinogens and psychotropics; and other substances and articles which present biological, chemical or radiological hazards to people and property.

The system is capable of rapidly and accurately discriminating among different substances and providing quantitative indication of the amount and location of a critical substance. As a result, it is highly adapted for use in applications that require high throughput and accuracy, such as security screening associated with airline and other forms of public transportation. The system provides for automated screening that can scan substantially the entire exterior surface of luggage and other hand-carried personal items, as well as cargo, without the need for hand wiping or sampling by an operator or other physical contact. As a result, the inevitable vagaries of human performance are virtually eliminated, improving the efficacy of detection. The present system is also useful for screening in other contexts, including courthouses, stadiums, schools, government offices, military installations, correctional institutions, and similar public venues that might be targets of terrorist or similar criminal activity. The combination of speed, accuracy, reliability, flexibility, low cost, and range of substances detectable solves problems associated with prior art scanning systems and renders the present invention highly advantageous. Furthermore, the present invention markedly reduces or eliminates false alarms while maximizing the probability of detection of actual contraband.

The present system is also capable of detecting the presence of contraband in a nondestructive manner, such that the surface being studied is left substantially undamaged as a result of being scanned by the present laser desorption system. That is, the appearance and function of the scanned surface is not harmed. Although in some cases, minimal changes may occur that are detectable only by microscopic or other sophisticated analytical means, the overall presentation of the article to the ordinary human senses is unaffected.

The present system is adapted for the detection of a wide variety of contraband substances for which detection is desired. The chemical analysis systems disclosed herein can be readily be adjusted and suitably calibrated and operated to be sensitive and selective for detection of such materials.

An analysis system incorporating a GC/IMS detector is especially versatile. It can detect both positively and negatively ionized molecules of many classes. Each species detectable therein has a particular and characteristic ionic mobility that affords selective detection.

The GC/IMS detector can readily be optimized to detect drugs and narcotics, including amphetamine-type stimulants such as methamphetamine, amphetamine, and ecstasy, cocaine, cannabis-containing substances including marijuana and hashish, and opiates including heroin and morphine.

The GC/IMS detector is also particularly useful for the detection of common aromatic and aliphatic organo-nitro compounds found very commonly in modern high explosives for which detection is sought.

The present system is particularly suited for the detection of modern plastic explosives such as C4, SEMTEX, and DM12 which are generally composed of particles of high explosives like RDX, PETN, and HMX in a sticky, polymeric matrix. These materials pose a grave threat in the hands of terrorists. Since the plastic explosives have little if any content of metals or other heavy elements, they exhibit little signature for x-ray detection. Moreover, they are available in a variety of physical forms, including moldable, clay-like substance and as thin sheets, making them relatively easy to disperse and hide among seemingly innocuous, ordinary objects. On the other hand, the propensity of plastic explosives to transfer residues to the hands of a user and to their environs provides avenues for detection that are uniquely exploited by the laser desorption system disclosed herein.

Referring to FIG. 1 of the drawings, there is depicted an explosive detection system 10 of the invention. A $CO_2$ gas laser 12 emits infrared laser light along optical path 14, which passes through focusing lens 16. The light strikes mirror 18, which is mounted on rotating shaft 19 of electric motor 20. The reflected light impinges on target 22 mounted on translation stage 24, which is movable by turning drive screw 26. Rotation of mirror 18 causes the point of impingement 28 of light on target 22 to move generally along a line 30 across target 22. Vapor and particles desorbed from target 22 are collected fill by vacuum 34 movably mounted on rail 36. A sample is collected on particle trap 38 mounted within vacuum 34 and analyzed by transferring it to an analyzer (not shown). In other embodiments the particle trap could be directly mounted on the analyzer or be located on a rotatable carousel allowing it to be selectively positioned for different functions, such as sample collection, analysis, and cleaning.

Figure 2:
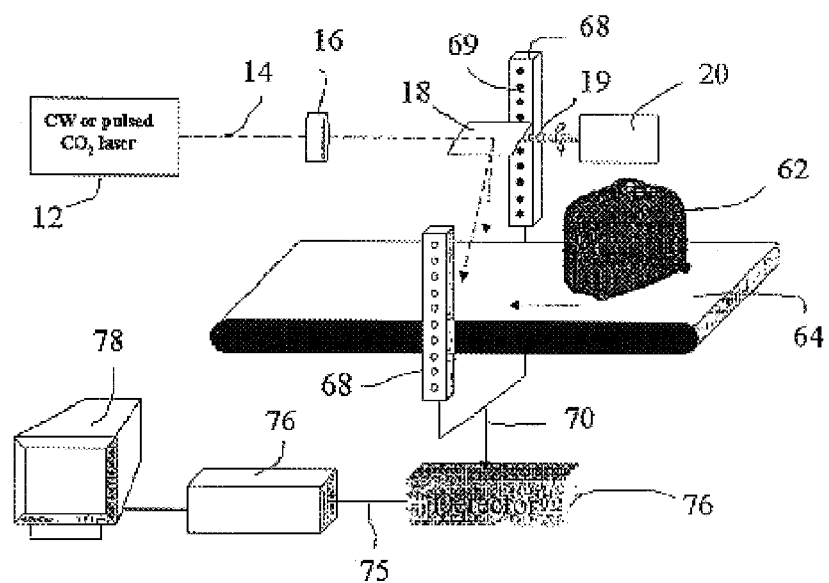
FIG. 2 is a perspective view of an automated explosive detection system for screening items of luggage.

In another aspect of the invention, depicted by FIG. 2, there is provided an automated explosive detection system 60 for screening items of luggage 62. A $CO_2$ gas laser 12 emits infrared laser light along optical path 14, which passes through an optical system comprising focusing lens 16 and mirror 18. The light strikes mirror 18, which is mounted on rotating shaft 19 of electric motor 20. Items of luggage 62 are placed on conveyor belt 64 appointed for motion along lengthwise direction 66. Rotation of mirror 18 causes the path of light reflected therefrom generally to traverse the width of conveyor belt 64. In operation of system 60, luggage 62 is conveyed to the region of traversal of light reflected from mirror 18. Upon impingement of light onto any point of luggage 62 at which contraband residue is present, vapor and/or particles thereof are desorbed in a plume that is collected by collection system 66 comprising vacuum heads 68 appointed for intake of the plume through inlet ports 69. Collection system 66 further comprises ducts 70 through which the plume is led. The plume enters chemical analysis system 72 comprising detector 74 adapted to detect the presence of at least one contraband substance. Detector 74 is connected by wire 75 to computer 76 associated with computer display terminal 78. Upon detection of a contraband substance, detector 74 outputs an electrical signal indicative of the detection to computer 76. Computer 76 is also operably connected to motor 20 and conveyor 64. Computer 76 is appointed to activate and control each of motor 20 and conveyor 64 and receive in real time signals indicative of the position and status of each. Software present and operable in computer 76 is appointed to operate motor 20 and conveyor 64 in a coordinated manner so as to raster scan the point of impingement of light reflected from mirror 18 onto luggage 62 to define an extended, two-dimensional interrogation zone. The raster scanning is carried out by simultaneously translating the luggage 62 longitudinally on conveyor belt 64 and transversely sweeping the light beam by rotating mirror 18. Signals fed in real time indicative of the positions of the conveyor belt and mirror are used by the software to provide real-time location of the light beam impingement and correlate it with the intensity of the contraband substance signal attributable to desorption from the corresponding region of the interrogation zone. The information may then be displayed as a mapping on computer display terminal 78 indicative of the positions on the luggage at which contraband is or is not detected. Preferably the mapping is displayed superimposed on a visual representation of the luggage to provide clear indication of the location on the actual article at which contraband is being detected.

The present explosive detection system affords a significant advance in its ability to indirectly detect explosives and other contraband concealed within luggage, packages, cargo, and the like. A very limited number of known explosive materials, e.g. nitroglycerin, have a sufficiently high room-temperature vapor pressure to cause emission of substantial vapor even if sequestered inside a package. However, other very common explosives carry equal or greater explosive energy; yet have vapor pressures that are orders of magnitude lower. As a result, materials posing enormous potential for harm, such as SEMTEX, DM12, and C-4, emit miniscule amounts of vapor whose concentration is too low to be detected by known methods. Most legitimate commercial and governmental producers of plastic explosives incorporate taggants having substantial vapor pressure such as dimethyldinitrobutane (DMNB) in plastic explosives to facilitate their tracing and enhance their detectability. The present system readily detects such taggants. However, illicit explosives made by terrorists or other criminal elements are highly unlikely to incorporate taggants. Moreover, the high volatility of taggants causes them to evaporate, often in a matter of minutes or a few hours, from trace sticky residues and/or contaminated fingerprints on the surface of items containing plastic explosives. The reliability of a luggage screening system that relies principally or exclusively on detection of taggants is thus dubious. The present system is highly advantageous in being able to detect residues of plastic explosives, whether or not so tagged. While it is highly likely that trace residues of the high explosive constituents are present on the surface of luggage or other parcel containing high explosive, enhancement in some form is still needed to assure their detectability. Prior art detection methods have relied on mechanical means, such as abrasion by a wipe or brush or a flow of gas to dislodge a sample large enough for analysis.

In contrast, the present system relies on impingement of thermal energy to desorb or ablate particles or vapor from the surface residue. The exact mechanism for the removal of material is not precisely known but is believed to depend on laser fluence and pulse length. A fluence ranging from about 1 to 50 $mJ/cm^2$ is presently believed suitable for the practice of the invention. At low fluences, the laser is believed to heat the material locally and raise its vapor pressure accordingly, causing thermal desorption of a plume containing principally monomers. At higher fluences (e.g., fluences >3.7 $mJ/cm^2$), it is believed that the ejection mechanism changes to ablation, in which sufficient heat is released to cause ablation of particles of material. In either case, a plume of vapor and/or particles is liberated that can be collected and transported to a chemical analysis detector system.

At low laser fluences thermal desorption from the surface is observed, the plume mostly contains monomers. At high fluences, the ejection mechanism changes to ablation, in which a volume of irradiated material is collectively ejected due to a phase explosion of the overheated material. Large clusters become a major constituent of the plume. At much higher fluences, several problems become apparent. Laser irradiation heretofore has generally been considered unsuitable for large-scale screening systems because of their propensity to cause perceptible damage to the substrate. Moreover, high fluence, especially in combination with long pulse duration, can produce local heating that is sufficient to cause substantial deflagration or detonation of explosive material on the surface of interest. It is preferred that the intensity and duration of the laser illumination used in the practice of the present invention not be sufficient to cause substantial deflagration or detonation of an explosive substance present on the surface being scanned. Excessive fluence may also cause decomposition of other substances of interest, such as drugs and narcotics, precluding their detection.

It is found that infrared laser radiation is effective in causing desorption of material such as explosive residues from a surface. A number of systems capable of lasing at infrared wavelengths are known, including Nd:YAG and $CO_2$ gas, and are suitable for practice of the invention. The effectiveness of laser radiation in causing desorption is enhanced by selection of a wavelength which the suspect material is known to absorb strongly. Incident radiation having a wavelength that overlaps the absorption band is strongly absorbed, leading to strong, selective heating of the substances of interest. Laser light having a wavelength at or near a peak in a material's absorption spectrum is especially effective. Consequently, one aspect of the present invention employs a $CO_2$ gas laser, which characteristically emits radiation at several frequencies in the 9–11 $\mu$m wavelength range. The C—$NO_2$ bond, present in virtually all nitrogenous explosives, has a substantial resonant absorption in this range, making it especially suited for use in a system for the detection of nitrogenous explosives according to the present invention.

Moreover, other materials, including the substrate, whose spectra do not exhibit strong absorption at the wavelength of the incident light, will not absorb substantially and so will not experience undue heating or other damage. Appropriate selection of wavelength thus affords selectivity, in that the material of interest is strongly and efficiently desorbed, while other materials are not markedly affected. The selectivity allows the intensity and duration of the illumination of the substrate by the laser light to be held at low levels, thereby eliminating damage to the substrate but still allowing efficient desorption of enough sample to allow reliable detection. This selectivity is highly advantageous for a screening system and overcomes the problems of surface damage heretofore presumed to be an inevitable consequence of laser illumination. The inventors have found that careful control of both laser wavelength and pulse duration and repetition rate is a highly effective means of maximizing the generation of the desired sample plume and minimizing collateral damage.

In addition, good selectivity enhances detection sensitivity by more efficiently removing desired substances, while virtually eliminating the removal of extraneous or background material, e.g., lint, dirt, or solvent, which frequently swamps detectors in prior art systems and results in the need for frequent cleaning of the collection and analysis systems. Conventional wipe-based systems are especially vulnerable to these difficulties. Laser desorption is also particularly effective in removing residue lodged in cracks and crevices of the substrate which are inaccessible by wiping.

The efficiency and selectivity of desorption may be further enhanced by altering the isotopic content of the $CO_2$ gas fill in the laser. It is known in the art that the spectral lines responsible for the laser action of a $CO_2$ gas laser entail molecular vibrations. Naturally occurring carbon is predominantly composed of atoms of a stable isotope having an atomic weight of about 12, denoted as $^{12}C$, with a slight amount of the stable isotope having atomic weight of about 13, or $^{13}C$, and lesser amounts of the unstable radioisotope $^{14}C$. Likewise, atmospheric oxygen is predominantly composed of diatomic $^{16}O_2$, with traces of $^{18}O_2$ and the mixed species $^{16}O^{18}O$. Thus, normal $CO_2$ is predominantly composed of $^{12}C$ and $^{16}O$, denoted as $^{12}C^{16}O_2$. However, techniques are known for the isotopic enrichment of both atoms, that is to say, the formation of a quantity of material in which the relative abundance of the various isotopes differs from the corresponding naturally occurring abundance. Thus, $CO_2$ gas enriched in any of the species $^{12}C^{16}O_2$, $^{13}C^{16}O_2$, $^{12}C^{18}O_2$, and $^{13}C^{18}O_2$ may be obtained. Laser action may be established in a $CO_2$ gas laser based on any of these species if present in sufficient concentration. The differences in atomic mass of the constituent atoms in each species give rise to a unique characteristic vibrational spectrum. Hence, laser operating frequencies not obtainable with normal $^{12}C^{16}O_2$ can be selected by altering the isotopic abundance in the gas charge. The efficiency and selectivity of desorption of a given contraband substance may be increased by selection of an illuminating wavelength matched as closely as possible to the particular absorption spectral lines of that substance. Thus, lasers based on $CO_2$ gas with different isotopes may be preferred for detecting particular contraband substances.

It will be recognized by those skilled in the art that the present detection system may employ multiple lasers or beam splitters to produce one or more additional beams. Use of multiple beams impinging different regions of a sample allows a plurality of locations to be screened simultaneously. In addition, the system may comprise multiple lasers operating at different wavelengths to enhance detection of different contraband substances preferentially desorbed at different wavelengths.

During practice of the present invention, the beam of light emitted from the laser is passed through an optical system that directs it to impinge on an interrogation area of the surface of the object to be analyzed. The optical system may comprise known optical components including apertures, lenses, mirrors, prisms, filters, and the like, appropriate for operation at the laser's wavelength. The system may be designed using principles known to those in the art. The optical system acts to focus the light to a spot size ranging from about 100 $\mu$m to 5 mm at the sample surface. The optical system may further include one or more deflecting optical components, such as a mirror, prism, diffraction grating, or other like means, at least one of which is moved to deflect the light beam, thereby changing the location at which the beam impinges on the surface of the object being scanned and creating an extended interrogation zone. Known electrical, pneumatic, or mechanical means may be used to impart linear or rotary motion to the component and thereby extend the interrogation zone. In one aspect, the beam is reflected from a rotating mirror affixed to the shaft of an electric motor to extend the interrogation zone.

The laser radiation used in practicing this invention may be emitted continuously. Preferably, the beam of light is pulsed. Such pulsing of the light beam is preferred because higher peak power and energy density can be employed without undesirable damage to the substrate or other similar thermal side effects. The use of a short pulse duration is preferred in that heating of the residue and underlying surface is thereby localized, minimizing or eliminating unwanted surface damage.

Pulsed beams may be obtained in several ways. Light from a continuously emitting laser may be passed through an interposed mechanical chopper, which may comprise a structure such as a disk, which has transparent portions and portions which are opaque to light having the wavelength of interest. The light beam is directed through the structure, which is rotated, as by an electric motor, to periodically interrupt the optical path. The repetition rate, pulse duration, and duty cycle may be varied by changing the rotational speed of the structure and the relative amounts of the structure that are transparent and opaque. Mechanical choppers generally have about a 50% duty cycle (i.e., the fraction of time during operation in which the chopper passes light). They are especially useful for obtaining pulse repetition rates of up to about 20 kHz. This rate is generally higher than may be obtained with a pulse-mode laser. Alternatively, electro-optic cells are known which may be made transparent or opaque in response to a suitable electrical input and operate at a higher pulse rate. A pulsed beam may be obtained by interposing such a cell in the optical path of the present system and providing a suitably varying electrical input, as would be known to one skilled in the art.

More preferably, a pulsed mode laser may be employed in the practice of the invention. $CO_2$ gas lasers are known which typically give pulse duration of about 200 ns and pulse repetition rates up to about 1 kHz.

The present system comprises a collection system for collecting vapor or particles of contraband analyte substances. The system may comprise a blower or mild or substantial vacuum system, one or more inlet ports, and associated ducting that directs the flow of analyte to substantially transfer it to the chemical analysis system.

The chemical analysis system comprises at least one detector sensitive to the presence of at least one of the contraband substances of interest, but may also comprise a plurality of detectors to make it sensitive to a wider range of substances. Detectors capable of operating in multiple modes may also be used.

In one aspect of the invention, the detector provides an electrical output signal representative of the detection of a contraband substance. Preferably the output signal has a magnitude that is proportional to the amount of a substance being detected. The detector may be adjusted and calibrated by an appropriate protocol, such as by establishing a background electrical output when it is known that no substance is actually present or by exposing the detector to a sample with a known concentration. It is then presumed that any signal above a preselected background level is indicative of the presence of a substance of interest. Alternatively, a background level may be determined dynamically during scanner operation by a known averaging protocol.

Indication of the detector signal output may be given by a wide variety of signal means known in the art. A binary "go/no go" indication may be provided using known comparator circuitry, in which the magnitude of the signal actually outputted by the detector is compared with a pre-selected detection threshold, and in response, audible or visible signals are activated, indicative of the presence or absence of a signal above the pre-selected threshold. The output of the detector may also be displayed as a quantitative reading on a digital or analog meter. A quantitative output may also be given by the intensity or color displayed on a monitor such as a computer display screen or terminal. Such a visual display is preferred for embodiments of the invention in which an extended, two-dimensional interrogation area is screened. In one aspect of the invention, a visual representation of the object being scanned is presented on a computer display screen and superimposed on the visual representation is a pattern or mapping, which, by variation of intensity or color, indicates the amount of contraband substance of a given type found on the corresponding area of the article surface. A mapping may use a false-color scheme to indicate different amounts detected. Alternatively, the presence of different contraband substances may be represented by different colors, intensity, or shading patterns.

A variety of detector systems may be incorporated in the chemical analysis system used in practice of the present invention.

A chemical analysis system incorporating a combined gas chromatograph/ion mobility spectrometer (GC/IMS) is especially preferred for the detection of explosive molecules. In this system particles and/or vapors desorbed by the laser system are drawn by a vacuum system onto a sample collector adapted to adsorb the analyte. The sample thus collected is transferred for injection into the GC/IMS. One suitable GC/IMS system is sold under the brand Orion™ by Scintrex Trace Corporation, Ottawa, Canada.

In some embodiments of the invention that entail a GC/IMS detector it is preferred to use a laser fluence large enough to cause some decomposition of explosive residues. Most organo-nitro explosives release $NO_2$ upon by decomposition, a product readily detected by a GC/IMS detector. Moreover, decomposition frequently results in a partially ionized plume. Such a partially ionized plume does not have to be ionized within the GC/IMS system itself, which relies on the mobility of an ionized molecular stream.

The chemical analysis system may also comprise a pyrolyzer/electrochemical sensor, which may operate in alternative sampling mode. In vapor mode, air is drawn by a vacuum system into a unit through a vapor absorber tube appointed to selectively absorb explosive vapor molecules. In particulate mode sample is first transferred to a sample screen and then inserted into the unit. The absorber tube is then rapidly heated by electrical or other means to convert organo-nitro based explosives molecules to simple by-product gases which are readily analyzed by the detector. The gases are picked up in an air stream and transferred to the detector. A signal is generated as the gases pass the detector's sensing surface, amplified, and passed to a microprocessor-based signal processing system. Based on the signal strength and delay time, the signal processing system recognizes the presence or absence of explosive vapor. This detector is also capable of detecting inorganic nitrate salts used as explosives, such as ammonium nitrate (AN) or mixtures of ammonium nitrate with fuel oil or the like (ANFO). One suitable system incorporating a pyrolyzer/electrochemical sensor is commercially available as an EVD3000™ system by Scintrex Trace Corporation, Ottawa, Canada.

In another aspect of the invention the chemical analysis system incorporates a gas chromatograph/surface surface ionization detection (GC/SID) detector. A sample is drawn into the analysis system and deposited onto a sample screen. The screen is then inserted into an inlet and heated to evaporate volatile material on the screen. The vaporized material is carried by an air flow generated by a pump into the gas chromatograph column. As molecules exit the column they are ionized by a hot filament and collected on a cathode. The resulting current is amplified and converted to a voltage signal by an electrometer. Each species has a characteristic time of passage, i.e. the interval between introduction of a molecule of that species into the gas chromatograph column and its detection at the column exit. A microprocessor-based signal processing system is used to sense the presence of a detected signal and the time of passage indicated thereby. A match between the known characteristic times of any of the molecules of contraband whose detection is sought and the actual times exhibited by molecules in a sample being analyzed is indicative of the presence of contraband in that sample. The microprocessor responds to determination of such a mach by activating a display on the control panel of the detector system. The display provides indication of the detection of contraband and its type. One suitable (GC/SID system is incorporated in the NDS2000™ unit sold by Scintrex Trace Corporation, Ottawa, Canada.

A variety of other detectors may be advantageously combined with the laser system described above for the practice of the present invention. They include gas chromatography/mass spectrometry (GC/MS), field ion spectrometry (FIS), photoacoustic detectors, and gas-phase infrared spectroscopy.

The present laser desorption and detection system may also be advantageously combined with other known scanning systems, such as magnetometric and x-ray systems. A system combining the detection methods can be made more compact and efficient, thereby satisfying the detection sensitivity and throughput required for screening of passengers and hand luggage in airports, for example.

The following examples are presented to provide a more complete understanding of the invention. The specific techniques, conditions, materials, proportions and reported data set forth to illustrate the principles and practice of the invention are exemplary and should not be construed as limiting the scope of the invention.

EXAMPLE 1

Test targets were made by dissolving a known quantity of explosive material in a solution, applying the solution to a substrate, and allowing the solution to dry. The amount of explosive present on the target was inferred from the amount of solution applied and the known concentration. The explosive RDX was dissolved in methanol/acetonitrile; the other samples were dissolved in pure methanol. The test targets are listed in Table I. The targets were each tested by placing them in a holder that allowed them to be illuminated by a pulsed $CO_2$ gas laser and to be translated. The plume evolved was tested. The laser was a 500 mJ/pulse unit operating in TEA mode. A 0.2 $cm^2$ aperture was interposed to limit the energy at the sample surface to a nominal value of 17 mJ. The pulse width was about 200 ns. The target was exposed to about 50 pulses of light distributed over the surface. The plume was drawn into a sampler situated about 10 cm from the focused spot. Sample was collected on a particle trap and subsequently analyzed for the presence of explosive with the detectors indicated, either an Orion GC/IMS detector or an EVD3000 pyrolyzer/electrochemical detector, both made commercially by Scintrex Trace Corporation.

TABLE I

| Sample No. | Substrate | Explosive | Detector |
| --- | --- | --- | --- |
| 1 | Boarding pass | RDX (1 µg) | Pyrolyzer/electrochemical |
| 2 | Glass slide | RDX (100 ng) | Pyrolyzer/electrochemical |
| 3 | Teflon | DM12 (1 µg) | Pyrolyzer/electrochemical |
| 4 | Teflon | DM12 (500 ng) | Pyrolyzer/electrochemical |
| 5 | Glass slide | RDX (1 ng) | GC/IMS |
| 6 | Polyester cloth | C4 (500 ng) | GC/IMS |
| 7 | Polyester-cotton cloth | C4 (500 ng) | GC/IMS |
| 8 | Leatherette | C4 (500 ng) | GC/IMS |
| 9 | Aluminum foil | C4 (500 ng) | GC/IMS |
| 10 | Glass Slide | C4 (500 ng) | GC/IMS |
| 11 | Floppy disk | C4 (500 ng) | GC/IMS |
| 12 | Polyethylene sheet | C4 (500 ng) | GC/IMS |

In each case, the presence of explosive material was detected reproducibly with a signal to noise ratio of at least about 50. The results demonstrate the ability of the system to detect the presence of explosive residues on a substrate without damage thereto.

EXAMPLE 2

Test targets were made an operator who handled various plastic explosives for one minute and then imposed his thumbprint onto the studied substrate. The test targets are listed in Table II. The targets were each tested as before by placing them in a holder that allowed them to be illuminated by a pulsed $CO_2$ gas laser and to be translated. The plume evolved was tested. The laser was a 500 mJ/pulse unit operating in TEA mode. A 0.2 $cm^2$ aperture was interposed to limit the energy at the sample surface to a nominal value of 17 mJ. The pulse width was about 200 ns. The target was exposed to about 50 pulses of light distributed over the surface. The plume was drawn into a sampler situated about 10 cm from the focused spot.

Sample was collected on a particle trap and subsequently analyzed for the presence of explosive with the detectors indicated, either an Orion GC/IMS detector or an EVD3000 pyrolyzer/electrochemical detector, both made commercially by Scintrex Trace Corporation. In the case of the plastic explosives, detection was based on the presence of organo nitro explosive, not on any taggant.

TABLE II

| Sample No. | Substrate | Explosive | Detector |
| --- | --- | --- | --- |
| 21 | Aluminum foil | Semtex H | Pyrolyzer/electrochemical |
| 22 | Boarding pass | Semtex H | Pyrolyzer/electrochemical |
| 23 | Polyethylene | Semtex H | Pyrolyzer/electrochemical |
| 24 | Leatherette | Semtex H | Pyrolyzer/electrochemical |
| 25 | Boarding pass | C4 | Pyrolyzer/electrochemical |
| 26 | Polyethylene | C4 | Pyrolyzer/electrochemical |
| 27 | Glass slide | C4 | Pyrolyzer/electrochemical |
| 28 | Glass slide | ANFO | Pyrolyzer/electrochemical |
| 29 | Aluminum foil | C4 | Pyrolyzer/electrochemical |
| 30 | Aluminum foil | DM12 | Pyrolyzer/electrochemical |
| 31 | polyethylene | C4 | Pyrolyzer/electrochemical |
| 32 | polyethylene | DM12 | Pyrolyzer/electrochemical |
| 33 | Aluminum foil | C4 | GC/IMS |
| 34 | Cardboard | C4 | GC/IMS |
| 35 | Black polyester | C4 | GC/IMS |
| 36 | Polyethylene | C4 | GC/IMS |

In each case, the presence of explosive material was detected reproducibly with a signal to noise ratio of at least about 50. The results demonstrate the ability of the system to detect the presence of explosive residues in contaminated fingerprints left on a substrate without causing damage thereto.

Having thus described the invention in rather full detail, it will be understood that such detail need not be strictly adhered to but that various changes and modifications may suggest themselves to one skilled in the art, all falling within the scope of the present invention as defined by the subjoined claims.

What is claimed is:

1. A method of detecting the presence of a preselected contraband substance on a surface of an object comprising the steps of:
   a. illuminating an interrogation area of said surface with a pulsed beam of light emitted from an infrared laser, said illumination having sufficient intensity and duration to cause selective ablation of molecules of said contraband substance present on said surface without substantially damaging said surface;
   b. collecting at least a portion of said desorbed molecules in a collection system;
   c. analyzing said portion in a chemical analysis system, the system being associated with said collection system and comprising a detector responsive to the presence in said chemical analysis system of said contraband substance;

d. outputting an electrical signal representative of said presence of said contraband substance; and e. activating signal means operably connected to said chemical analysis system in response to the output of said electrical signal.

2. A method as recited by claim 1, wherein said light is pulsed by a chopper interposed in said beam.

3. A method as recited by claim 1, wherein said laser is a pulsed laser.

4. A method as recited by claim 1, wherein said pulses have a duration ranging from about 5 femtoseconds to 500 microseconds.

5. A method as recited by claim 1, wherein said pulses have a repetition rate ranging from about 10 to 20,000 Hz.

6. A method as recited by claim 5, wherein said $CO_2$ gas in said laser is isotopically enriched.

7. A method as recited by claim 1, wherein said beam has a spot size on said surface ranging from about 0.1 to 5 mm.

8. A method as recited by claim 1, wherein said laser has a fluence ranging from about 0.5 to 50 ml/cm$^2$.

9. A method as recited by claim 8, wherein said explosive agent comprises an organo-nitro explosive compound.

10. A method as recited by claim 8, wherein said contraband substance comprises an inorganic nitrate salt explosive agent.

11. A method as recited by claim 1, wherein said laser is a $CO_2$ gas laser.

12. A method as recited by claim 1, wherein said contraband substance comprises an explosive agent.

13. A method as recited by claim 12, wherein said explosive agent comprises a plastic explosive.

14. A method as recited by claim 1, wherein said contraband substance comprises a narcotic agent.

15. A method as recited by claim 1, wherein said contraband substance comprises a chemical agent.

16. A method as recited by claim 1, wherein said detector is a GC/IMS detector.

17. A method as recited by claim 1, wherein said detector is a pyrolysis electrochemical detector.

18. A method as recited by claim 1, wherein said detector is a surface ionization detector.

19. A method as recited by claim 1, further comprising relative motion of said object and said beam of light to illuminate an extended interrogation zone.

20. A method as recited by claim 19, wherein said optically deflecting component is a rotating mirror.

21. A method as recited by claim 19, further comprising moving said object on a conveyor belt.

22. A method as recited by claim 19, wherein said beam of light is raster scanned over said extended interrogation zone.

23. A method as recited by claim 19, further comprising displaying a mapping on a computer display terminal, said mapping being indicative of the location at which a contraband substance has been detected.

24. A method as recited by claim 1, further comprising movably deflecting said light with an optically deflecting component to illuminate an extended interrogation zone.

25. A method as recited by claim 1 wherein said intensity and duration of said illumination is not sufficient to cause substantial deflagration or detonation of said substance present on said surface.

26. An apparatus for non-destructively detecting the presence of a contraband substance on a surface of an object comprising:

a. an infrared laser adapted to emit light;

b. an optical system adapted to deliver a pulsed beam of said light emitted from said infrared laser to illuminate an interrogation area of said surface, said illumination having sufficient intensity and duration to cause selective ablation of molecules of said contraband substance present on said surface without substantially damaging said surface;

c. a collection system adapted to collect at least a portion of said desorbed molecules;

d. a chemical analysis system associated with said collection system and having a detector responsive to the presence in said collection system of said desorbed molecules and adapted to output an electrical signal representative of said presence of said contraband substance; and e. signal means operably connected to said chemical analysis system and responsive to the output of said electrical signal.

27. The apparatus of claim 26, further comprising a chopper interposed in said beam.

28. The apparatus of claim 26, wherein said laser is a pulsed laser.

29. The apparatus of claim 26, wherein said pulses have a duration ranging from about 5 femtoseconds to 500 microseconds.

30. The apparatus of claim 26, wherein said pulses have a repetition rate ranging from about 10 to 20,000 Hz.

31. The apparatus of claim 26, wherein said light has a spot size on said surface ranging from about 0.1 to 5 mm.

32. The apparatus of claim 26, wherein said laser is a $CO_2$ gas laser.

33. The apparatus of claim 32, wherein said $CO_2$ gas isotopically enriched.

34. The apparatus of claim 26, wherein said contraband substance comprises an explosive agent.

35. The apparatus of claim 34, wherein said explosive agent comprises an organo nitro explosive compound or inorganic nitrate salt.

36. The apparatus as recited by claim 34, wherein said explosive agent comprises a plastic explosive.

37. The apparatus of claim 34, wherein said explosive agent comprises an inorganic nitrate salt.

38. The apparatus of claim 26, wherein said contraband substance comprises a narcotic agent.

39. The apparatus of claim 26, wherein said contraband substance comprises a chemical agent.

40. The apparatus of claim 26, wherein said detector is a GC/IMS detector.

41. The apparatus of claim 26, wherein said detector is a pyrolysis electrochemical detector.

42. The apparatus of claim 26, wherein said detector is a surface ionization detector.

43. The apparatus of claim 26, wherein said optical system comprises at least one deflecting optical component and means for imparting motion thereto, the motion of said defecting optical component changing the location at which said beam impinges on said surface, thereby extending said interrogation zone.

44. The apparatus of claim 43, further comprising translation means adapted to move said object.

45. The apparatus of claim 44, wherein said translation means comprises a conveyor belt.

46. The apparatus of claim 44, wherein said beam is raster scanned over said interrogation zone.

47. The apparatus of claim 44, further comprising:

a. a computer operably connected to said detector, said drive motor, and said translation means;

b. a computer display terminal associated with said computer;
c. said computer being adapted to control the operation of said drive motor and said translation means; and
d. said computer further being adapted to display on said computer display terminal a mapping representative of the positions on said surface at which said contraband substance is detected.

48. The apparatus of claim 26, further comprising translation means adapted to move said object.

49. An apparatus as recited by claim 26, wherein said intensity and duration of said illumination is not sufficient to cause substantial deflagration or detonation of said substance present on said surface.

50. An apparatus as recited by claim 26, wherein said detector is a GC/MS detector.

51. An apparatus as recited by claim 26, wherein said detector is an FIS detector.

52. An apparatus as recited by claim 26, wherein said detector is a gas-phase infrared detector.

53. An apparatus as recited by claim 26, wherein said detector is a photoacoustic detector.

* * * * *